US010959932B2

(12) United States Patent
Daep et al.

(10) Patent No.: US 10,959,932 B2
(45) Date of Patent: Mar. 30, 2021

(54) MUCIN COATED SILICA FOR BACTERIAL AGGREGATION

(71) Applicant: Colgate-Palmolive Company, New York, NY (US)

(72) Inventors: Carlo Daep, Brooklyn, NY (US); Michael Fitzgerald, Oakhurst, NJ (US); Ekta Makwana, Monroe, NJ (US); Peter R. Hilliard, Jr., Far Hills, NJ (US); Shamim Ansari, Princeton, NJ (US); Robert D'Ambrogio, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 11 days.

(21) Appl. No.: 16/067,014

(22) PCT Filed: Dec. 30, 2016

(86) PCT No.: PCT/US2016/069419
§ 371 (c)(1),
(2) Date: Jun. 28, 2018

(87) PCT Pub. No.: WO2017/117500
PCT Pub. Date: Jul. 6, 2017

(65) Prior Publication Data
US 2019/0015313 A1    Jan. 17, 2019

Related U.S. Application Data

(60) Provisional application No. 62/273,105, filed on Dec. 30, 2015.

(51) Int. Cl.
*A61K 8/64* (2006.01)
*C01B 33/149* (2006.01)
*A61Q 11/00* (2006.01)
*A61K 8/02* (2006.01)
*A61K 9/00* (2006.01)
*A61K 8/44* (2006.01)
*A61K 8/25* (2006.01)
*A61K 6/54* (2020.01)
*A61K 47/60* (2017.01)
*A61K 8/21* (2006.01)
*A61K 8/27* (2006.01)
*A61K 38/17* (2006.01)
*A61K 9/16* (2006.01)

(52) U.S. Cl.
CPC .............. *A61K 8/64* (2013.01); *A61K 6/54* (2020.01); *A61K 8/02* (2013.01); *A61K 8/0241* (2013.01); *A61K 8/21* (2013.01); *A61K 8/25* (2013.01); *A61K 8/27* (2013.01); *A61K 8/44* (2013.01); *A61K 9/006* (2013.01); *A61K 9/0063* (2013.01); *A61K 38/1735* (2013.01); *A61K 47/60* (2017.08); *A61Q 11/00* (2013.01); *C01B 33/149* (2013.01); *A61K 9/0053* (2013.01); *A61K 9/1611* (2013.01); *A61K 2800/412* (2013.01)

(58) Field of Classification Search
CPC ... A61K 8/44; A61K 8/21; A61K 8/64; A61K 47/60; A61K 8/25; A61K 9/0063; A61K 8/0241; A61K 38/1735; A61K 8/02; A61K 8/27; A61K 9/006; A61K 6/54; A61K 9/0053; A61K 9/1611; A61K 2800/412; A61Q 11/00; C01B 33/149; C08L 1/00
See application file for complete search history.

(56) References Cited

U.S. PATENT DOCUMENTS

| | | | |
|---|---|---|---|
| 4,339,432 A * | 7/1982 | Ritchey | A61K 8/27 424/49 |
| 5,849,876 A | 12/1998 | Linsley et al. | |
| 6,319,513 B1 | 11/2001 | Dobrozsi | |
| 7,659,240 B2 | 2/2010 | Kadiyala et al. | |
| 8,221,724 B2 * | 7/2012 | Hughes | A61K 8/25 424/49 |
| 8,287,843 B2 * | 10/2012 | Boyd | A61Q 11/00 424/49 |
| 9,192,914 B2 | 11/2015 | Miyahara et al. | |
| 9,320,699 B2 | 4/2016 | Porter et al. | |
| 2001/0038831 A1 | 11/2001 | Park et al. | |
| 2002/0037259 A1 | 3/2002 | Budny | |
| 2003/0166535 A1 * | 9/2003 | Podolsky | A61K 38/22 514/2.4 |
| 2010/0316580 A1 * | 12/2010 | Kohli | A61K 33/16 424/52 |
| 2011/0064815 A1 | 3/2011 | Strugala et al. | |
| 2012/0328682 A1 * | 12/2012 | Bardwell | A01N 25/08 424/405 |

(Continued)

FOREIGN PATENT DOCUMENTS

| | | |
|---|---|---|
| CN | 102006874 A | 4/2011 |
| CN | 102821739 A | 12/2012 |
| CN | 103906708 A | 7/2014 |

OTHER PUBLICATIONS

Pettersson et al., "Normal and friction forces between mucin and mucin—chitosan layers in absence and presence of SDS", Journal of Colloid and Interface Science, vol. 324, Issues 1-2, Aug. 2008, pp. 246-256.*
Meyer-Leuckel et al., Effect of mucin alone and in combination with various dentifrices on in vitro Remineralization, Caries Research, Sep.-Oct., 38(5)m 478-483, 2004 (Year: 2004).*
International Search Report and Written Opinion of the International Searching Authority in International Application No. PCT/US2016/069419, dated Mar. 30, 2017.

(Continued)

*Primary Examiner* — Lezah Roberts

(57) ABSTRACT

Disclosed herein is mucin-coated silica, compositions comprising the same, and methods of promoting the aggregation and/or clearance of oral bacteria using such compositions.

16 Claims, No Drawings

(56) References Cited

U.S. PATENT DOCUMENTS

2016/0193124 A1  7/2016 Porter et al.

OTHER PUBLICATIONS

Pettersson, 2008, "Lubrication and Surface Properties of Adsorbed Layers of Polyelectrolytes and Proteins," KTH Chemical Science and Engineering Doctoral Thesis, http://www.diva-portal.org/smash/get/diva2:13308/FULLTEXT01.pdf.

Svensson, 2008, "Interactions of Mucins with Biopolyrners and Drug Delivery Particles," Malmo University, Health and Society Doctoral Dissertations, https://dspace.mah.se/bitstream/handle/2043/5930/Olof%20Svensson%20Kappan.pdf?sequence=1.

* cited by examiner

MUCIN COATED SILICA FOR BACTERIAL AGGREGATION

BACKGROUND

Oral cavity bacteria are the primary cause of dental ailments, including caries, gingivitis, periodontitis, and halitosis. Oral bacteria form biofilms which are tightly adhered to the oral surfaces, especially the tooth enamel. With time these biofilms calcify and turn into tartar, making them more difficult to remove from the tooth surface. Current at-home dental treatments, such as tooth brushing and mouth rinsing, can provide only marginal benefit in preventing the growth of oral biofilm, or preventing the conversion of biofilm to plaque and tartar. The only effective way to remove plaque and tartar once it has formed is through costly, sometimes uncomfortable professional dental treatments such root planning and scaling. It would be extremely beneficial to develop means of preventing the initial formation of oral bacterial biofilms before the process of plaque and tarter formation has begun.

The formation of oral biofilm requires the interaction of a variety of proteins and sugars on the surface of bacterial cells. After a successful dental cleaning, much of the oral biofilm may be removed, which leaves the teeth ready for a new round of bacterial colonization and the development of a new biofilm. The first step in biofilm formation is colonization by primary colonizers, which include *Streptococcus* species (e.g., *S. oralis, S. mutans, S. sanguinis, S. mitis* and *S. gordonii*), allowing the eventual accumulation of secondary organisms that are typically associated with oral health problems. Therefore, it would be of great benefit to be able to interfere with these organisms' ability to initiate attachment to the oral surfaces, preventing the eventual formation and accumulation of oral biofilms.

Mucins are a family of high-molecular weight glycoproteins that are produced by mucosal epithelial cells throughout the human body. They are a predominant ingredient of secretions of the respiratory tract (e.g., mucus) and of saliva. Many species of bacteria readily associate with mucins by utilizing it as a natural substrate for oral surface colonization. Therefore, mucins have the ability to aggregate bacteria.

If mucins could be anchored to an insoluble support, such as insoluble particles, then such mucin-coated particles could serve as a target for bacterial attachment and adherence. Rinsing the oral cavity using a composition comprising such particles would then be a way of collecting loose bacteria in the oral cavity for elimination.

BRIEF SUMMARY

It has now been discovered that small-particle silica can be surface-functionalized with mucin to yield mucin-coated silica particles. These mucin-coated silica particles are able to adhere bacteria in the oral cavity, enabling the bacteria to be effectively eliminated. Regular use of oral care products containing such mucin-coated silica would serve as a way to prevent the development of oral biofilms by aggregating and eliminating oral bacteria before they can form extensive biofilm.

This aggregation and elimination of oral bacteria can result in multiple favorable effects on oral hygiene and oral health, including reduction and inhibition of acid erosion of the enamel, cleaning of the teeth, reduction of bacterially-generated biofilm and plaque, reduction of gingivitis, inhibition of tooth decay and inhibition of the formation of cavities. The method comprises the application of a composition of the present disclosure to the teeth.

The present disclosure provides mucin-coated silica particles, methods of preparing mucin-coated silica particles, oral care compositions comprising mucin-coated silica particles, and method of using such compositions for the prevention and/or treatment of conditions of the oral cavity. Mucin-coated silica particles can be formulated directly into various oral care delivery systems, such as liquid mouthwash, liquigel, and both aqueous and non-aqueous gel or paste dentifrices. In some embodiments, mucin-coated particles can be entrapped or encapsulated in various matrices for release during use of the composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The present disclosure provides, in a first aspect, mucin-coated silica particles for use in an oral care composition. In preferred embodiments, the silica has an average particle size of 20 microns or less. Silica particles are coated by a surface layer of mucin by incubating the silica particles in a solution of mucin (e.g., purified or recombinant human, bovine or porcine mucin). It has been found by the inventors that the primary determinant of binding is the surface area of the silica particles, rather than the size (e.g., diameter) of the silica particles. Mucin becomes adsorbed to the surface of the silica particles by extensive hydrogen bonding interactions between the hydrophilic protein and sugar moieties of the mucin molecules and the hydrophilic oxygen backbone of the silica particles. Bacteria are then able to aggregate to the mucin, and by extension, to the silica.

Mucins are glycosylated proteins (glycoconjugates) produced by the epithelial tissues of most animals. Mucins are composed of three distinct regions: an amino terminal region which is lightly glycosylated and rich in cysteine; a large central region formed of multiple tandem repeats (e.g., 10-80 residue sequences in which up to 50% of the resides are serine or threonine) which are heavily O-glycosylated (also with some N-glycosylation); a carboxy terminal region which is lightly glycosylated and rich in cysteine.

Mucilage is a thick, adhesive substance produced by most plants and some microorganisms. It can be a glycoprotein or a polysaccharide in nature. Cacti and other succulent plants and flax seeds are a particularly rich source of mucilage. Certain plant species produce significantly more mucilage than others. These high-mucilage plants include far greater concentrations of mucilage than is typically found in most plants: *Aloe vera, Basella alba* (Malabar spinach), *Cactus, Chondrus crispus* (Irish moss), *Corchorus* (jute plant), *Dioscorea polystachya* (nagaimo, Chinese yam), *Drosera* (sundews), *Drosophyllum lusitanicum,* Fenugreek, Flax seeds, Kelp, Liquorice root, Marshmallow, Mallow, Mullein, Okra, *Parthenium, Pinguicula* (butterwort), *Psyllium* seed husks, *Salvia hispanica* (chia) seed, *Talinum triangulare* (waterleaf), *Ulmus rubra* bark (slippery elm), and *Plantago major* (greater plantain). Another good source of exopolysaccharide mucilage is green algae, especially Volovcales family species, as well as marine mucilage, such as that produced by phytoplankton.

As used throughout the present disclosure, the term "mucin" includes both animal-derived mucin and plant- or microorganism-derived mucilage. In some embodiments, the mucin is only animal-derived mucin. In other embodiments, the mucin is either plant-derived mucilage or microorganism-derived mucilage, or a mixture thereof. When the mucin is animal-derived mucin, it may be mucin derived from any vertebrate animal species, including, fish, amphibians, reptiles, birds or mammals.

In one embodiment, the silica used for the mucin-coating is small-particle silica. Silica particles having an average particle size of 8 microns or less are commercially available silicas such as PQ Corporation (formerly from INEOS) SORBOSIL AC43 (SORBOSIL AC43 is a silica with properties including a powder RDA of 160, an oil absorption coefficient of 75 cm3/100 g, a weight mean particle size of 3.5 microns, an ignition loss at 1000° C. of 11.0% max, and a pH of 5.5). Another useful silica is silica with properties including an average particle size of 2.7-4.0 microns (as determined by MALVERN MASTERSIZER), a sieve residue of +45 μm, a moisture loss at 105° C. of 8.0% max, an ignition loss at 1000° C. of 14.0% max, and a pH of 5.5-7.5 in aqueous suspension), available from Ineos Silicas, Warrington, United Kingdom. Another embodiment of the invention is a silica with an average particle size of 1.5-6.0 microns.

Other possible silicas for mucin-coating include typical abrasive silicas, such as precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 105, 114, 115, 119 and 165. Some of these silica abrasives are described in U.S. Pat. No. 4,340,583, incorporated herein by reference. In certain embodiments, abrasive materials useful in the practice of the oral compositions in accordance with the invention include silica gels and precipitated amorphous silica having an oil absorption value of less than 100 cc/100 g silica and in the range of 45 cc/100 g to 70 cc/100 g silica. Oil absorption values are measured using the ASTA Rub-Out Method D281. Low oil absorption silica abrasives useful include those marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight and an oil absorption of less than 70 cc/100 g of silica is an example of a low oil absorption silica abrasive useful in the present disclosure.

In some embodiments, the mucin-coated silica comprises silica of an average particle size of less than 20 microns, for example, 1-20 microns, 1-16 microns, 2-16 microns, 1-6 microns, 2-5 microns, 8-16 microns, 8-15 microns, 8-12 microns, or 10-16 microns, or a combination thereof (e.g., a population consisting of silica of 2-5 micron average size and 8-12 micron average size). As used herein throughout, references to silica size, surface area, porosity and other physical characteristics refer to the said characteristics of the silica particles in absence of mucin-coating.

Surface area is an important characteristic in determining the extent to which mucin will adsorb onto the silica. In some embodiments, the silica particles used in preparation of the mucin-coated silica have an $N^2$ BET surface area of at least 25 $m^2/g$, or at least 50 $m^2/g$, or at least 100 $m^2/g$. In some embodiments, the silica particles have an $N^2$ BET surface area of 25-100 $m^2/g$, or 50-150 $m^2/g$, or 25-500 $m^2/g$, or 50-500 $m^2/g$, or 100-500 $m^2/g$, or 100-400 $m^2/g$, or 200-400 $m^2/g$, or 200-500 $m^2/g$, or 300-400 $m^2/g$, or 100-200 $m^2/g$.

In some preferred embodiments, the silica particles used in preparation of the mucin-coated silica have an $N^2$ BET of 200-500 $m^2/g$ or 300-400 $m^2/g$ and an average particle size of 1-16 microns or 2-5 microns. In other embodiments, the silica particles used in preparation of the mucin-coated silica have an $N^2$ BET of 30-50 $m^2/g$ or 50-70 $m^2/g$ and an average particle size of 8-12 microns or 8-15 microns. In still other embodiments, the silica particles used in preparation of the mucin-coated silica have an $N^2$ BET of 25-100 $m^2/g$ or 30-70 $m^2/g$ and an average particle size of 5-20 microns or 8-15 microns. In still other embodiments, the silica particles used in preparation of the mucin-coated silica have an $N^2$ BET of 100-200 $m^2/g$ or 100-150 $m^2/g$ and an average particle size of 5-20 microns or 10-15 microns. In still other embodiments, the silica particles used in preparation of the mucin-coated silica is selected from the group consisting of silica having: an $N^2$ BET of 360-410 $m^2/g$ and an average particle size of 2-25 microns; an $N^2$ BET of 30-50 $m^2/g$ and an average particle size of 8-12 microns; an $N^2$ BET of 50-70 $m^2/g$ and an average particle size of 8015 microns; or an $N^2$ BET of 100-160 $m^2/g$ and an average particle size of 10-16 microns; or combinations thereof.

Mammalian mucins are available from a variety of sources, such as different species (e.g., human, porcine, bovine) and different epithelial cavities within those species (e.g., gastric, respiratory, salivary). Mucins may be obtained by purification from natural animal sources, or by the use of recombinant DNA technology. The particular mucin may be chosen based on such factors as cost, availability, purity, immunogenicity, hydrophilicity, molecular weight and extent of glycosylation. The adsorption of mucin to silica depends on electrostatic, hydrogen bonding and other non-covalent interactions that depend on the nature of the glycoproteins in the mucin. Preferred mucins include bovine submaxillary mucin, porcine submaxillary mucin, and porcine gastric mucin. For example, powdered Type II porcine gastric mucin is available from Sigma-Aldrich (St. Louis, Mo.).

Loading of mucin on silica can range from about 0.1 mg/100 mg silica to 10 mg/100 mg silica (1:1000 to 1:10 w). In some embodiments, the loading ranges from about 0.5 mg/100 mg silica to about 5 mg/100 mg silica. In some embodiments, the average mucin loading is about 1 mg/100 mg silica to 2 mg/100 mg/silica, or about 1 mg/100 mg silica.

The total amount of mucin bound to the silica can be determined by using absorption spectroscopy at 215 nm and/or 225 nm.

In a second aspect, the present disclosure provides an oral care composition (Composition 1), such as a dentifrice, e.g., a toothpaste, comprising mucin-coated silica particles, as described above. Such a composition may comprise from 0.1-50 wt % of mucin-coated silica particles, e.g., 1-50 wt %.

In additional embodiments, the present disclosure provides oral care compositions as follows:
1.1. Composition 1, wherein the composition further comprises a basic amino acid, e.g., lysine or arginine, in free or orally acceptable salt form.

1.2. Composition 1 or 1.1, wherein the composition further comprises a metal salt, e.g., zinc salt, copper salt or stannous salt (e.g., zinc oxide, zinc citrate, zinc lactate, zinc phosphate, or a combination thereof).

1.3. Any of the foregoing compositions in the form of a toothpaste, gel, mouthwash, powder, cream, strip (e.g., thin films), or gum.

1.4. Any of the foregoing compositions in an orally acceptable base, e.g., a mouthwash, gel, or dentifrice base.

1.5. Any of the foregoing compositions in the form of a dentifrice, wherein the mucin-coated silica particles are present in an effective amount to inhibit oral biofilm formation, e.g., present in an amount of from 0.1 to 20% by weight of the composition, or 0.5 to 15%, 0.5 to 10%, 1 to 10%, 2 to 8%, 3 to 5%, or about 3%, or about 5% or about 8% or about 10%.

1.6. Any of the foregoing compositions, wherein the composition comprises a dentifrice base further comprising an abrasive, e.g., an effective amount of a silica, calcium abrasive, e.g., 10-30%, e.g., about 20%.

1.7. Any of the foregoing compositions in the form of an oral gel, wherein the mucin-coated silica particles are present in an effective amount to inhibit oral biofilm formation, e.g., present in an amount of from 0.1 to 20% by weight of the composition, or 0.5 to 15%, 0.5 to 10%, 1 to 10%, 2 to 8%, 3 to 5%, or about 3%, or about 5% or about 8% or about 10%.

1.8. Any of the foregoing compositions further comprising an effective amount of a fluoride ion source, e.g., providing 50 to 3000 ppm fluoride.

1.9. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.10. Any of the preceding compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.

1.11. Any of the foregoing compositions comprising buffering agents, e.g., phosphate buffers or citrate buffers, for example, sodium phosphate buffer (e.g., sodium phosphate monobasic, disodium phosphate and/or phosphoric acid).

1.12. Any of the foregoing compositions comprising a humectant, e.g., selected from glycerin, sorbitol, propylene glycol, polyethylene glycol, xylitol, and mixtures thereof, e.g. comprising at least 10%, e.g., 10-70%, or 20-50%, or 20-40%, e.g., 25-35% or 50-70%, of humectant or humectant mixture.

1.13. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropylbetaine, e.g. in an amount of from about 0.1% to about 4.5% by weight, e.g. 0.5-2% cocamidopropylbetaine.

1.14. Any of the preceding compositions further comprising a viscosity modifying amount of one or more of polysaccharide gums, for example xanthan gum or carrageenan, silica thickener, and combinations thereof.

1.15. Any of the preceding compositions comprising gum strips or fragments.

1.16. Any of the preceding compositions further comprising flavoring, fragrance and/or coloring.

1.17. Any of the foregoing compositions comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, magnolol, honokiol, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan, or cetylpyridinium chloride or magnolol or honokiol.

1.18. Any of the preceding compositions further comprising a whitening agent, e.g., a selected from the group consisting of peroxides, metal chlorites, perborates, percarbonates, peroxyacids, hypochlorites, and combinations thereof.

1.19. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.20. Any of the preceding compositions, further comprising an agent that interferes with or prevents bacterial attachment, e.g., solbrol or chitosan.

1.21. Any of the preceding compositions, further comprising a source of calcium and phosphate selected from (i) calcium-glass complexes, e.g., calcium sodium phosphosilicates, and (ii) calcium-protein complexes, e.g., casein phosphopeptide-amorphous calcium phosphate 1.22. Any of the preceding compositions, further comprising a soluble calcium salt, e.g., selected from calcium sulfate, calcium chloride, calcium nitrate, calcium acetate, calcium lactate, and combinations thereof.

1.23. Any of the preceding compositions further comprising a physiologically or orally acceptable potassium salt, e.g., potassium nitrate or potassium chloride, in an amount effective to reduce dentinal sensitivity.

1.24. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.

1.25. Any of the foregoing compositions, further comprising a non-ionic polymer, e.g. polyvinylpyrrolidone (PVP), for example linear or cross-linked PVP.

1.26. Any of the preceding compositions further comprising a breath freshener, fragrance or flavoring.

1.27. Any of the foregoing compositions, wherein the pH of the composition is approximately neutral, e.g., from pH 5 to 10, or from pH 6 to pH 8 e.g., about pH 7.

1.28. Any of the foregoing compositions, wherein the mucin is entrapped or encapsulated within a matrix in the oral care composition, for example, a polymer matrix (e.g., a matrix formed from any of the polymers described herein or any combination thereof).

As used herein, the term "dentifrice" include both aqueous and non-aqueous toothpastes and tooth gels, as well as aqueous liquigels, mouthwashes (including structured mouthwashes), beads, films, flosses, tapes, and gums. A liquigel formulation can be formulated as a liquigel toothpaste or as a "paint-on" liquigel.

In another aspect, the present disclosure provides a method (Method 1) of promoting the aggregation and/or clearance of oral bacteria, comprising administering to the oral cavity of a person an oral care composition (Composition 1, et seq.) comprising mucin-coated silica particles. In some embodiments, Method 1 is effective in treating diseases, disorders and conditions of the oral cavity, such as gingivitis, periodontitis, halitosis, cavity formation, enamel erosion, and oral infection (e.g., oral candidiasis), or to disrupt the formation of dental plaque, dental tartar and/or bacterial biofilm. For example, where Composition 1, et seq., is a toothpaste composition, Method 1 would comprise the steps of brushing the teeth with the toothpaste composition for a sufficient amount of time (e.g., from 1-4 minutes, preferably 2-4 minutes), followed by rinsing the oral cavity with water, optionally followed by rinsing the oral cavity with a mouthwash. The brushing step serves to provide close contact of the mucin-coated silica particles with the oral bacteria and biofilm, while the mechanical brushing action serves to dislodge and release oral bacteria from the teeth and biofilm allowing for their aggregation and adherence to the mucin-coated silica particles. The rinsing steps allow for the elimination of these mucin-coated silica/bacteria aggregates or complexes, thus ridding the oral cavity of bacteria.

In a second embodiment, the present disclosure provides a method (Method 2) of treating a disease, disorder or condition of the oral cavity, comprising the step of administering to a patient in need thereof an oral care composition (Composition 1, et seq.) comprising mucin-coated silica particles to promote the aggregation and/or clearance of oral bacteria. In specific embodiments, said patient suffers from a disease, disorder or condition of the oral cavity, such as gingivitis, periodontitis, halitosis, cavity formation, enamel erosion, and/or oral infection (e.g., oral candidiasis). For example, where Composition 1, et seq., is a toothpaste composition, Method 1 would comprise the steps of brushing the teeth with the toothpaste composition for a sufficient amount of time (e.g., from 1-4 minutes, preferably 2-4 minutes), followed by rinsing the oral cavity with water, optionally followed by rinsing the oral cavity with a mouthwash. The brushing step serves to provide close contact of the mucin-coated silica particles with the oral bacteria and biofilm, while the mechanical brushing action serves to dislodge and release oral bacteria from the teeth and biofilm allowing for their aggregation and adherence to the mucin-coated silica particles. The rinsing steps allow for the elimination of these mucin-coated silica/bacteria aggregates or complexes, thus ridding the oral cavity of bacteria.

In some embodiments, the oral bacteria aggregated by the uses and methods disclosed herein include one or more of *Streptococcus* species (e.g., *S. oralis, S. mutans, S. sanguinis, S. mitis* and *S. gordonii*). In some embodiments, the patients administered the compositions according to Method 1 or Method 2 have demonstrated one or more of *Streptococcus* species in their oral cavities which are contributing to poor oral health. In some embodiments, the patients administered the compositions according to Method 1 or Method 2 have been diagnosed with an oral bacterial disease or disorder, e.g., an oral bacterial infection caused by one or more of *Streptococcus* species. In some embodiments, the patients administered the compositions according to Method 1 or 2 are suffering from conditions or recovering from treatments that predispose them to oral bacterial infections (e.g., periodontitis, gingivitis, oral surgery, tooth extraction, root canal treatment), such as infection by *Streptococcus* species.

In some embodiments, Method 1 or 2 further provides effectiveness to reduce and inhibit acid erosion of the enamel, clean the teeth, reduce bacterially-generated biofilm and plaque, reduce gingivitis, inhibit tooth decay and formation of cavities, and reduce dentinal hypersensitivity. In some embodiments, the Methods allow for the aggregation and destruction of oral bacteria transiently released from the oral surfaces (e.g., the bacterial biofilm of the teeth) before they can reattach to solid structures in the oral cavity.

In some embodiments, the present disclosure provide a method according to Method 1 or 2, which is effective for one or more of the following: (i) to reduce hypersensitivity of the teeth, (ii) to reduce plaque accumulation, (iii) to reduce or inhibit demineralization and promote remineralization of the teeth, (iv) to inhibit microbial biofilm formation in the oral cavity, (v) to reduce or inhibit gingivitis, (vi) to promote healing of sores or cuts in the mouth, (vii) reduce levels of acid producing bacteria, (viii) to increase relative levels of non-cariogenic and/or non-plaque forming bacteria, (ix) to reduce or inhibit formation of dental caries, (x) to reduce, repair or inhibit pre-carious lesions of the enamel, e.g., as detected by quantitative light-induced fluorescence (QLF) or electrical caries measurement (ECM), (xi) to treat, relieve or reduce dry mouth, (xii) to clean the teeth and oral cavity, (xiii) to reduce erosion, (xiv) to whiten teeth; (xv) to reduce tartar build-up, (xvi) to freshen the breath and/or treat or prevent halitosis, and/or (xvii) to promote systemic health, including cardiovascular health, e.g., by reducing the potential for systemic infection via the oral tissues, the method comprising applying any of Compositions 1, et seq. as described above to the oral cavity of a person in need thereof, e.g., one or more times per day. The present disclosure further provides Compositions 1, et seq. for use in any of these methods.

The present disclosure further provides the use an oral care composition (Use 1) comprising mucin-bound silica particles (e.g., Composition 1, et seq.) to promote the aggregation of oral bacteria and/or to promote the clearance of oral bacteria, for example, in Method 1 or Method 2, as described above. In some embodiments, the use of Composition 1, et seq., to promote the aggregation and/or clearance of oral bacteria is effective in treating diseases, disorders or conditions of the oral cavity (e.g., gingivitis, periodontitis, halitosis, cavity formation, enamel erosion, or oral infection) or in disrupting the formation of plaque and bacterial biofilm. In specific embodiments, said use is effective to reduce and inhibit acid erosion of the enamel, clean the teeth, reduce bacterially-generated biofilm and plaque, reduce gingivitis, inhibit tooth decay and formation of cavities, and/or reduce dentinal hypersensitivity.

The oral care composition used in the present disclosure can be in the form of any oral care formulations, including a toothpaste, gel, mouthwash, powder, cream, strip, gum, bead, film, floss or any other known in the art. In some embodiments, the oral care composition used in the present disclosure is a toothpaste or oral gel. In some embodiments, the oral care composition is a liquid mouthwash, liquigel, aqueous or non-aqueous gel or paste dentifrice. In some embodiments, the oral care composition is structured mouthwash. In some embodiments, the oral care composition is an aqueous liquigel toothpaste or a "paint on" liquigel formulation.

In another aspect, the present disclosure provides the use of mucin-coated silica particles in the manufacture of an oral care composition for use in Method 1 or Method 2, e.g., for use in promoting the aggregation of oral bacteria and/or promoting the clearance of oral bacteria. Such use may be beneficial for the treatment and/or prevention of a disease or disorder of the oral cavity, as described elsewhere herein, caused by said oral bacteria.

In some embodiments, the methods and uses disclosed herein (Method 1, Method 2, and Use 1), may further comprise the administration of an antibacterial agent to provide a synergistic increase in antibacterial effect. This synergistic effect may arise from the ability of the mucin-coated silica to promote bacterial aggregation and biofilm disruption, thus increasing the ability of the antibacterial agent to access the bacterial cells. Any antibacterial agent disclosed herein may be useful for said synergistic effect, including but not limited to, quaternary ammonium compounds (e.g., cetyl pyridinium chloride), halogenated diphenyl ethers (e.g., triclosan), and magnolia extracts (e.g., magnolol, honokiol).

In some embodiments, the oral care compositions (Composition 1, et seq.) may further comprises a basic amino acid. Basic amino acids are known to have many beneficial effects in the treatment and prevention of oral care diseases and disorders, such as a reduction in cariogenic bacteria and/or an increase in arginolytic bacteria.

By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In certain embodiments, the amino acid is lysine. In other embodiments, the amino acid is arginine.

In certain embodiments, zinc is present in the oral care composition used in the present disclosure in an amount of 0.05 to 10% by weight of the composition. In other embodiments, the amount of zinc is at least 0.1, at least 0.2, at least 0.3, at least 0.4, at least 0.5, at least 1, at least 2, at least 3, or at least 4 up to 10% by weight of the composition. In other embodiments, the amount of the zinc is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, the oral care composition used in the present disclosure is anhydrous. By anhydrous, there is less than 5% by weight water, optionally less than 4, less than 3, less than 2, less than 1, less than 0.5, less than 0.1 down to 0% by weight water.

Active Agents: The oral care composition used in the present disclosure may comprise various agents which are active to protect and enhance the strength and integrity of the enamel and tooth structure and/or to reduce bacteria and associated tooth decay and/or gum disease, including or in addition to the mucin-coated silica particles. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 wt % (expressed as weight of free base), e.g., about 1 to about 10 wt % for a consumer toothpaste or about 7 to about 20 wt % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly, with levels used in toothpaste being e.g., about 5 to about 15 times greater than used in mouthrinse. For example, a triclosan toothpaste may contain about 0.3 wt % triclosan.

Fluoride Ion Source: The oral care composition used in the present disclosure may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition described herein may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions described herein at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

Abrasives: The oral care composition used in the present disclosure, e.g. Composition 1 et seq., may include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Foaming agents: The oral care composition used in the present disclosure also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the composition. Polyoxyethylene is also commonly known as polyethylene glycol ("PEG") or polyethylene oxide. The polyoxyethylenes suitable for this composition will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions. Where present, the amount of of foaming agent in the oral care composition (i.e., a single dose) is about 0.01 to about 0.9% by weight, about 0.05 to about 0.5% by weight, and in another embodiment about 0.1 to about 0.2% by weight.

Surfactants: The oral care composition used in the present disclosure may contain anionic surfactants, for example:
i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
ii. higher alkyl sulfates, such as sodium lauryl sulfate,
iii. higher alkyl-ether sulfates, e.g., of formula $CH_3(CH_2)_m CH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH_2)_2OSO_3Na$).
iv. higher alkyl aryl sulfonates such as sodium dodecyl benzene sulfonate (sodium lauryl benzene sulfonate)
v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The oral care composition used in the present disclosure may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the compositions described herein, e.g., Composition 1, et seq., comprises sodium lauryl sulfate.

The surfactant or mixtures of compatible surfactants can be present in the compositions described herein in about 0.1% to about 5.0%, in another embodiment about 0.3% to about 3.0% and in another embodiment about 0.5% to about 2.0% by weight of the total composition.

Tartar control agents: In various embodiments, the oral care composition used in the present disclosure may comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The composition thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP)($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Polymers: The oral care composition used in the present disclosure may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present in the oral care composition used in the present disclosure. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The oral care composition used in the present disclosure may include an anionic polymer, for example in an amount of from about 0.05 to about 5%. Such agents useful in compositions described herein are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Water: The oral care composition used in the present disclosure may comprise significant levels of water. Water employed in the preparation of commercial oral compositions should be deionized and free of organic impurities. The amount of water in the compositions includes the free water which is added plus that amount which is introduced with other materials.

Humectants: In certain embodiments, it is also desirable to incorporate in the oral care composition used in the present disclosure a humectant to prevent the composition from hardening upon exposure to air. Certain humectants can also impart desirable sweetness or flavor to dentifrice compositions. Suitable humectants include edible polyhydric alcohols such as glycerin, sorbitol, xylitol, propylene glycol as well as other polyols and mixtures of these humectants. In some embodiments of the composition described herein, the principal humectant is glycerin, which may be present at levels of greater than 25%, e.g. 25-35% about 30%, with 5% or less of other humectants.

Unless stated otherwise, all percentages of composition components given in this specification are by weight based on a total composition or formulation weight of 100%.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1: Preparation and Analysis of Mucin-Coated Silica

A variety of silica particle types are incubated with porcine gastric mucin at a concentration of 1 mg/mL. A stock solution of 1 mg/mL mucin is prepared by adding 1 gram of powdered Type II porcine gastric mucin to 1 L of boiling deionized water and stirring until it is dissolved. After cooling to room temperature, 100 mg of silica is added to 10 mL of mucin solution and the mixture is stirred for 30 minutes. The resulting suspension is then centrifuged at 4000 rpm for one minute, and the supernatant solution is decanted. The collected silica is washed twice with deionized water by stirring, centrifuging and decanting. The collected mucin-coated silica is finally stored under 1 mL of deionized water to prevent drying out (thus, 100 mg/mL suspension of mucin-coated silica). Typical properties of the silicas tested are shown in Table 1.

TABLE 1

| Property | AC43 | Zeo105 | Zeo114 | Zeo 165 | BFG50 |
|---|---|---|---|---|---|
| $N^2$ BET Surface Area ($m^2/g$) | 360-410 | 30-50 | 50-70 | 100-160 | NA |

TABLE 1-continued

| Property | AC43 | Zeo105 | Zeo114 | Zeo 165 | BFG50 |
|---|---|---|---|---|---|
| CTAB (m$^2$/g) | <50 | 25-45 | 45-65 | 220-250 | NA |
| Oil Absorption (cc/100 g) | 70-90 | 50-65 | 95-110 | 160-230 | 60-80 |
| Avg. Particle size (μm) | 2 to 5 | 8 to 12 | 8 to 15 | 10 to 16 | 200 to 350 |
| Einlehner hardness | 23 to 27 | 12 to 18 | <5 | <3 | <5 |
| RDA-Abrasivity (20% loading) | 135-160 | 160-200 | 85-105 | NA | NA |
| PCR-Cleaning Potential (20% loading) | 90-120 | 90-105 | 70-85 | NA | NA |

After centrifuging to remove unbound mucins, the silica solids are washed with deionized water. A sample of the resulting silica is subjected to ultraviolet spectroscopy at both 215 and 225 nm wavelength. The result are shown in Table 2. AC43 silica is shown to have the greatest absorption of mucin under these conditions. It is also found that surface area, rather than particle size, is the key determinant of mucin loading on the silica particles.

TABLE 2

Adsorption of Mucin to Silica

| Silica Type | % of Total Mucin Adsorbed |
|---|---|
| No Silica | 0 |
| Zeo105 | 6 |
| BFG50 | 10 |
| Zeo114 | 11 |
| Zeo165 | 14 |
| AC43 | 17.5 |

Example 2: Clearance of *Streptococcus gordonii* Bacteria by Mucin-Coated Silica Green-fluorescent protein (GFP)-expressing *Streptococcus gordonii* is cultured in brain-heart infusion broth supplemented with 1% w/v yeast extract and 50 μg/mL (w/v) erythromycin at 37° C. under a 5% carbon dioxide atmosphere for 24 hours. The expression of GFP results in the visualization of the bacteria by fluorescence microscopy using an excitation wavelength of 488 nm and an emission wavelength of 519 nm.

After centrifuging and washing to remove the growth medium, the bacterial culture is resuspended and adjusted to an optical density (610 nm) of about 0.8 in phosphate buffered saline (PBS). Into the first well (well A) of a 24-well polystyrene dish is inoculated 1.5 mL of the resulting bacterial suspension. Into a second well (well B), 5 mg of mucin-coated silica prepared according to Example 1 is inoculated. Into a third well (well C), 1.5 mL of bacterial suspension pretreated with 5 mg of mucin-coated silica is inoculated. The 24-well plate is then incubated at 37° C. for two hours on a shaker at 100 rpm.

The suspension from each well is aspirated and each well is washed with 1 mL of sterile PBS three times. Bright-field photomicrographs are taken. Well A shows an abundance of small, brightly lit bacterial rods throughout the field. Well B shows no bacteria, but shows an abundance of irregularly shaped silica particles which are significantly larger than the bacteria of well A but are much less brightly lit. Well C, in contrast, shows an abundance of silica particles which are brightly lit, but few if any isolated bacteria. This demonstrates that all or nearly all of the bacterial cells from the culture have adhered to the silica particles, thus giving them apparent brightness. This changed brightness of the silica particles demonstrates that the bacteria has become bound to the surface of the silica particles.

Example 3: Reduced Recovery of *Streptococcus gordonii* Bacteria After Incubation with Mucin-Coated Silica After additional rinsing of wells A, B and C from Example 2 to remove the silica particles, leaving only surface-adhered bacteria, the bacteria are collected, plated on tryptic soy agar supplemented with 5% sheep blood, and incubated at 37° C. under a 5% carbon dioxide atmosphere for 16 hours. The number of colony forming units (CFUs) of *S. gordonii* is then calculated. The results are shown in Table 3. There is approximately a 90% decrease in bacterial recovery after incubation with mucin-coated silica.

TABLE 3

Bacterial Recovery After Incubation with Mucin-Coated Silica

| | Recovered *S. gordonii* CFUs |
|---|---|
| *S. gordonii* | 77000 |
| Mucin-silica complex | 0 |
| *S. gordonii*/Mucin-silica complex | 8600 |

Example 4: Reduced Surface Adherence of *Streptococcus gordonii* Bacteria After Incubation with Mucin-Coated Silica In an experiment similar to Example 2, 200 μL of bacterial suspension, or about 1 mg of mucin-coated silica, or both, are dispensed into clear-bottom polystyrene plates and incubated at 37° C. under a 5% carbon dioxide atmosphere with shaking at 100 rpm. After washing the wells to remove the silica, confocal microscopy is conducted. The wells incubated with bacteria only shows the presence of large numbers of GFP-tagged bacteria. This is shown by overlying the confocal image with the fluorescent image, as it demonstrates that each of the visible bacterial cells fluoresce green. In contrast, the wells incubated with mucin-coated silica followed by washing show neither visible bacteria nor GFP fluorescence. Surprisingly, the wells incubated with both bacteria and mucin-coated silica, following washing away of the silica, shows a nearly complete absence of both visible bacteria and GFP fluorescence. In fact, the images taken from these wells are nearly indistinguishable from those taken from the silica-only wells. This data further demonstrates the ability of mucin-coated silica to adhere bacteria and remove bacteria by rinsing away of the silica particles. Table 4 further shows fluorescence quantification of these results. The amount of GFP fluorescence detected in the wells in which mucin-coated silica and GFP-expressing bacteria were incubated together is essentially the same as the fluorescence in the negative control.

TABLE 4

Reduced Biomass After Incubation with Mucin-Coated Silica

|  | Averaged relative fluorescence units |
|---|---|
| S. gordonii only | 4.09 |
| Silica + Mucin | 1.401 |
| Silica + Mucin + S. gordonii | 1.43 |

Example 5: Bacterial Attachment to AC43 Silica Assessed by Fluorometry

The adherence of GFP-expressing *Streptococcus gordonii* to both free AC43 silica and mucin-coated AC43 silica is determined by fluorometry at an excitation wavelength of 488 nm and an emission wavelength of 519 nm emission). The results are shown in Table 5. Data is normalized against the negative control (mucin-coated silica only) to differentiate mucin auto-fluorescence (indicated by the broken red line) from the fluorescence signal associated with bacterial GFP. The observed increase in fluorescence in both free silica and mucin-coated silica controls indicates that bacterial adherence with increased fluorescence correlated with increased bacterial binding to the tested substrates. While bacterial adherence to the bare silica surface is observed, increased bacterial attachment is observed when *S. gordonii* is combined with the mucin-coated silica substrate. The most bacterial adherence is observed after a 15 minute incubation with the mucin-coated silica.

TABLE 5

Bacterial Attachment to Silica

|  | Relative Fluorescence Units |
|---|---|
| Silica only (w/o bacteria) | 2967 |
| Silica + Mucin (w/o bacteria) | 8863 |
| Silica only 5-min (Pellet after treatment) | 12968 |
| Silica + Mucin 5 min (Pellet after treatment) | 15464 |
| Silica only 15-min (pellet after treatment) | 12657 |
| Silica + Mucin 15 min (pellet after treatment) | 22410 |

Example 6: Oral Care Composition Comprising Mucin-Coated Silica Particles

Mucin-coated synthetic amorphous silica can be incorporated into the following dentifrice compositions for use in the methods described herein:

TABLE 6

| MATERIAL | FORMULA | | |
|---|---|---|---|
|  | A | B | C |
| SORBITOL - 70% SOLUTION | 15.00 |  | 41.51 |
| 99.0%-101.0% GLYCERIN | 16.00 | 29.70 | 20.00 |
| POLYETHYLENE GLYCOL 600 | 3.00 |  | 3.00 |
| DEMINERALIZED WATER | Q.S. | Q.S | Q.S |
| SYNTHETIC AMORPHOUS SILICA ABRASIVE (e.g., AC43) | 10.00 | 5.00 | 3.00 |
| SYNTHETIC AMORPHOUS SILICA ABRASIVE (e.g., Z 114) |  | 10.00 | 10.00 |
| SYNTHETIC AMORPHOUS SILICA THICKENER (e.g. Z 165) | 8.00 | 3.50 | 3.00 |
| SODIUM MONOFLUOROPHOSPHATE |  |  | 1.10 |
| SODIUM FLUORIDE | 0.243 | 0.243 |  |
| ANTIBACTERIAL AGENT |  | 0.300 |  |
| GANTREZ | 2.00 | 2.00 |  |
| POTASSIUM NITRATE | 5.00 |  |  |
| POTASSIUM CITRATE |  |  | 5.04 |
| FLAVOR | 1.10 | 1.05 | 1.00 |
| SODIUM SACCHARIN | 0.40 | 0.30 | 0.27 |
| SODIUM CMC | 0.40 | 1.30 | 0.60 |
| XANTHAN GUM | 0.17 |  | 0.17 |
| CARRAGEENAN |  | 0.60 |  |
| SODIUM LAURYL SULFATE POWDER | 1.50 | 1.50 | 1.20 |
| POLOXAMER 407 | 1.00 |  |  |
| SODIUM HYDROXIDE 50% | 1.45 | 1.20 |  |
| Sodium Phosphate, Tribasic, Hydrate | 1.00 |  |  |
| TITANIUM DIOXIDE | 1.00 | 0.50 | 0.10 |
| COLOR |  |  | 0.001 |
| Total Components | 100.000 | 100.000 | 100.000 |

Example 7: Structured Mouthrinse

Mucin-coated particles can be suspended in a mouthrinse structured with a combination of xanthan and gellan gums. A structured mouthrinse formulation containing AC43 silica particles is made and is found to remain intact in high water systems after three months of aging at both controlled room temperature and accelerated (40° C. and 75% relative humidity) conditions. It is found that a static yield stress of at least 0.3 Pa is effective in providing a homogenous suspension of particles in the continuous phase, despite such particles having a higher density than the continuous mouthrinse phase (particle density about 1.5 g/mL, versus continuous phase density of about 1.0 g/mL).

Formulas "A" and "B" of Table 7, below, demonstrate effective levels of gellan and xanthan materials to provide the necessary yield stress for a homogenous suspension of silica particles. In contrast, formula "C" of Table 7 is not structured, and is thus not capable of prolonged suspension of the mucin-coated silica particles. It is further found that the presence of divalent or monovalent metal ion salts (such as calcium chloride or sodium chloride) help control the viscosity of the mouthrinse within the preferred range of 200-1,000 cps. Preferably, buffers control the pH of the mouthrinse to between 5 and 7. Viscosity and Yield Stress (YS) are measured at room temperature with a V73 spindle at 1 rpm.

TABLE 7

| Formula | A | B | C |
|---|---|---|---|
| Demineralized water | Q.S | Q.S | Q.S |
| Glycerin | 4.90 | 4.90 | 4.90 |
| Propylene Glycol | 4.44 | 4.44 | 4.44 |
| Sodium Chloride | 0.86 | 0.29 | 0.86 |
| Mucin-coated Silica | 0.50 | 0.50 | 0.50 |
| Polysorbate 20 | 0.49 | 0.49 | 0.49 |
| Poloxomer 407 | 0.49 | 0.49 | 0.49 |
| Sodium Benzoate | 0.49 | 0.49 | 0.49 |
| 85% Syrupy Phosphoric Acid | 0.39 | 0.39 | 0.39 |
| Low Acyl Gellan Gum | 0.14 | 0.12 | 0.00 |
| Xanthan Gum | 0.11 | 0.09 | 0.00 |
| Cetylpyridinium Chloride | 0.075 | 0.075 | 0.075 |
| Sodium Fluoride | 0.05 | 0.05 | 0.05 |
| Flavor | 0.21 | 0.21 | 0.21 |
| Color | 0.001 | 0.001 | 0.001 |
| Initial Viscosity (cps)/YS (Pa) | 520/0.44 | 255/0.30 | 405/0 |
| Viscosity (cps)/YS (Pa) at 3 Mo | 595/0.49 | 390/0.32 | 435/0 |

TABLE 7-continued

| Formula | A | B | C |
|---|---|---|---|
| Physical Stability after 3 months @ RT | Pass - Particles homogenous & intact | Pass - Particles homogenous & intact | Fail - Particles intact but settled at bottom |

Example 8: Aqueous Liquigel Toothpaste

The mucin-coated particles are formulated in a liquigel formulation which can be dispensed on a toothbrush, as shown in Table 8 below. It is found that this formula remains physically stable after three months of aging at accelerated conditions. In this formula, the silica particles are similar to the specific gravity of the toothpaste continuous phase and a homogenous distribution is maintained during storage. The static yield stress of this formula, provided by low concentrations of silica thickener and xanthan, contributes to suspension of mucin-coated silica particles as well. The formula has a viscosity targeted between 5,000 and 60,000 cps, and a pH between 7 and 9.

TABLE 8

| Formula | D |
|---|---|
| Sorbitol, 70% Aq. | 42.50 |
| Demineralized Water | Q.S. |
| Glycerin | 12.00 |
| Mucin-coated Silica | 10.00 |
| Ppt. Silica Thickener | 3.30 |
| Sodium Lauryl Sulfate | 1.50 |
| Cocoamidopropyl Betaine (30% Aq) | 1.25 |
| Flavor | 1.50 |
| Tetrasodium Pyrophosphate | 0.50 |
| Sodium CMC | 0.26 |
| Titanium Dioxide | 0.25 |
| Sodium Fluoride - | 0.24 |
| Xanthan Gum | 0.18 |
| Viscosity (×10,000 cps)/YS (Pa) @ 25 C./60% RH, 1 rpm, V73 spindle | |
| Initial | 12/27 |
| 3 Months | 27/35 |
| Specific Gravity | 1.29 |
| Physical Description | Physically stable, homogenous, free flowing (requires no more than about 0.5 bar squeeze pressure exerted on toothpaste tube) gel |

Example 9: Paint-On Liquigel

The mucin-coated particles can also be formulated in a liquigel formulation without water which can be either "painted" or swabbed directly on teeth with a specifically designed applicator brush. A representative formula is shown in Table 9 below

TABLE 9

| Formula | E |
|---|---|
| Dimethylpolysiloxane-trimethylated silica co-polymer | 30.50 |
| Cross linked Polyvinyl pyrrolidone | 20.00 |
| Dimethylpolysiloxane | 16.00 |
| Sorbitan sebacate behamate polymer | 14.00 |
| Mucin-coated Silica | 15.00 |
| Fumed Silica | 3.00 |

TABLE 9-continued

| Formula | E |
|---|---|
| Flavor | 1.00 |
| Sodium Saccharin | 0.50 |
| Viscosity (×10,000 cps)/YS (Pa) @ 25 C./60% RH, 1 rpm, V73 spindle | |
| Initial | 413/38 |
| 3 Months | 524/55 |
| Specific Gravity | 1.33 |
| Physical Description | Physically stable, homogenous gel of low viscosity |

Example 10: Bead

The mucin-coated particles can also be encapsulated in a bead or capsule, which is particularly useful for application with a portable device (e.g., one designed with a divot in the brush head for placing an oral care bead, e.g., of approximately 5 mm in diameter). Upon brushing, the bead is broken down with mechanical action and the mucin-coated particles are released in the oral cavity. A formulation containing approximately 10-30% concentration of mucin-coated silica is preferred for this application due to the lesser dosage ultimately delivered per brushing via a single bead. However, these beads are not intended to be expectorated while brushing "on-the-go" so will be retained in the oral cavity for a longer time compared to some other applications. A representative bead formula is shown in Table 10.

TABLE 10

| Formula | F |
|---|---|
| Microcrystalline Cellulose | 40.00 |
| Mucin-coated Silica | 30.00 |
| Demineralized Water | Q.S. |
| Glycerin | 10.00 |
| Sodium Alginate | 5.00 |
| Polysorbate 80 | 1.00 |
| Titanium Dioxide | 1.00 |
| Calcium Chloride | 1.00 |
| Sodium Saccharin | 0.50 |
| Flavor | 0.50 |
| Physical Description | Spherical semi-soft bead approximately 5 mm diameter |

Example 11: Film

The mucin-coated particles can also be encapsulated in a strip or film which can (when cut to smaller pieces) be added to any of the formulations described herein or can be placed directly into the mouth to be dissolved on contact with saliva (i.e., as a portable oral care option). As with the beads, these strips are not intended to be expectorated when used as a portable option so the mucin-coated silica will theoretically be retained in the oral cavity for a longer time compared to a toothpaste application. A strip formula is shown in Table 11.

TABLE 11

| Formula | G |
|---|---|
| Hydroxypropyl Methylcellulose | 50.00 |
| Mucin-coated Silica | 30.00 |
| Propylene Glycol | 10.00 |
| Canola Oil | 5.00 |

TABLE 11-continued

| Formula | G |
|---|---|
| Polysorbate 80 | 2.00 |
| Titanium Dioxide | 2.00 |
| Saccharin | 0.50 |
| Flavor | 0.50 |
| Physical Description | White film |

Example 12: Floss

The mucin-coated particles can also be embedded on the surface of a dental floss for increased cleaning potential. The particles provide a source of abrasion on initial contact of the floss to hard tissue and is then released with mechanical action during flossing to provide a means of collecting loose bacteria in the oral cavity for elimination. U.S. Pat. No. 8,967,161 (incorporated herein by reference in its entirety) describes dental floss compositions of an elastomeric matrix and containing one or more particles. Such a dental floss could easily be adapted for this present application with mucin-coated particles incorporated at 2% or greater concentration on the floss surface. Other "traditional" floss substrates could also potentially be used in combination with the silica particles.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

What is claimed is:

1. An oral care composition comprising from 0.1 to 50% by weight of mucin-coated silica particles; wherein the silica has a $N^2$ BET surface area of 360 to 410 $m^2/g$, and an oil absorption (cc/100 g) of 70 to 90, and Einlehner hardness of 23 to 27, and RDA abrasivity at 20% loading of 135 to 160 and an average particle size of 2 to 5 microns.

2. The oral care composition of claim 1, wherein the oral care composition comprises from 0.1 to 20% by weight of mucin-coated silica particles, or comprises from 0.5 to 15% by weight of mucin-coated silica particles.

3. The oral care composition of claim 1, further comprising zinc oxide or a metal salt, wherein the metal salt comprises a zinc salt, a copper salt or a stannous salt.

4. The oral care composition of claim 3, wherein the zinc salt is selected from: zinc citrate, zinc lactate, zinc phosphate, and a combination thereof.

5. The oral care composition of claim 1, further comprising a basic amino acid, wherein the basic amino acid is selected from lysine and arginine, and is in free or orally acceptable salt form.

6. The oral care composition of claim 1, in the form of a toothpaste, gel, mouthwash, powder, cream, strip, thin films, or gum.

7. The oral care composition of claim 1, in the form of a toothpaste, gel or mouthwash.

8. The oral care composition of claim 1, further comprising an effective amount of a fluoride ion source, providing 50 to 3000 ppm fluoride.

9. A method of promoting the aggregation and/or clearance of oral bacteria, comprising administering to the oral cavity of a person an oral care composition according to claim 1.

10. The method of claim 9, wherein the method is effective in treating diseases, disorders and conditions of the oral cavity, such as gingivitis, periodontitis, halitosis, cavity formation, enamel erosion, and oral infection (e.g., oral candidiasis), or to disrupt the formation of dental plaque, dental tartar and/or bacterial biofilm.

11. A method of treating a disease, disorder or condition of the oral cavity, comprising the step of administering to a patient in need thereof an oral care composition according to claim 1, to promote the aggregation and/or clearance of oral bacteria, optionally, wherein said patient suffers from a disease, disorder or condition of the oral cavity, such as gingivitis, periodontitis, halitosis, cavity formation, enamel erosion, and/or oral infection (e.g., oral candidiasis).

12. The oral care composition according to claim 1, wherein the mucin-coated silica comprises from 0.1 to 10 mg of mucin per 100 mg of silica.

13. The oral care composition according to claim 12, wherein the mucin-coated silica comprises about 1 mg of mucin per 100 mg of silica.

14. The oral care composition according to claim 1, wherein the mucin is selected from: animal-derived mucin; plant-derived mucilage; and microorganism-derived mucilage.

15. The oral care composition according to claim 1, wherein the mucin is selected from: bovine submaxillary mucin; porcine submaxillary mucin; porcine gastric mucin; and a combination thereof.

16. The oral care composition according to claim 15, wherein the mucin comprises porcine gastric mucin.

* * * * *